United States Patent [19]

Rosenstein

[11] Patent Number: 5,024,239

[45] Date of Patent: Jun. 18, 1991

[54] METHOD AND APPARATUS FOR DETERMINING OSSEOUS IMPLANT FIXATION INTEGRITY

[76] Inventor: Alexander D. Rosenstein, 31862 Coast Hwy. Ste. 302, Laguna, Calif. 92677

[21] Appl. No.: 463,427

[22] Filed: Jan. 11, 1990

Related U.S. Application Data

[63] Continuation of Ser. No. 290,240, Dec. 21, 1988, abandoned.

[51] Int. Cl.$^5$ .................... A61B 5/103; A61B 7/00; A61B 5/00; G01H 13/00
[52] U.S. Cl. .................... 128/774; 128/773; 128/739; 73/582
[58] Field of Search .................... 128/739–740, 128/773, 774, 660.06; 73/579, 582, 588, 662; 324/635, 636

[56] References Cited

U.S. PATENT DOCUMENTS 4,502,329  3/1985  Fukunaga et al. .................... 73/579
4,754,763  7/1988  Doemland .................... 128/739

FOREIGN PATENT DOCUMENTS 2156983  10/1985  United Kingdom .................... 128/897

OTHER PUBLICATIONS

R. Schroeer, 'The Acoustic Impact Technique', Jun. '70, pp. 194–196.

Primary Examiner—Max Hindenburg
Assistant Examiner—Robin R. Longo
Attorney, Agent, or Firm—Bernard L. Kleinke; William Patrick Waters; Jerry R. Potts

[57] ABSTRACT

An apparatus for detecting loosening of an implant imbedded in a bone of a limb of a patient, includes a vibrator is pressed into engagement with the limb to impart vibratory motion to the bone. The vibrator is controlled to cause the vibratory motion to have a predetermined recurring pattern. A pickup device is pressed into engagement with the limb spaced from the vibrator over the same bone near the implant, for detecting the vibratory motion transmitted through the bone implant composite to generae an output signal. Implant loosening is determined when the recurring pattern of the output signal transmitted through the bone implant composite demonstrates sustained superimposition on the oscilloscope and/or significant secondary harmonics on the spectrum analyzer.

13 Claims, 3 Drawing Sheets

Output waveform from a firmly implanted prosthesis.

Frequency analysis of the waveform from a firmly implanted prosthesis.

Output waveform from a loose prosthesis.

Frequency analysis of the waveform from a loose prosthesis.

METHOD AND APPARATUS FOR DETERMINING OSSEOUS IMPLANT FIXATION INTEGRITY

This is a continuation of application Ser. No. 07/290,240, filed on Dec. 21, 1988, abandoned.

TECHNICAL FIELD

The present invention relates, in general, to diagnostic methods and apparatus for determining the integrity of bone implants and, more particularly, to diagnostic methods and apparatus for detecting the loosening of a cemented femoral hip implant.

BACKGROUND ART

Total hip replacement is one of the most commonly performed orthopedic procedures. In such a procedure, the acetabulum of the hip is replaced with a cup-shaped socket device which receives and articulates with a prosthetic femoral implant which consists of a ball portion and a stem portion which inserted fixedly in the femur. The femur is the longest bone in the skeleton, and is almost perfectly cylindrical in the greater part of its extent. At its proximate portion are the head, the neck, a greater trochanter and a lesser trochanter. The head is globular and generally hemispheric in shape. The surface of the femur head is smoothly contoured and, under normal conditions, moves freely within the acetabulum of the hip.

The neck of the femur is a pyramidal process of bone connecting the head with the femur body, disposed at approximately a 135° angle relative to the shaft of the bone. The greater trochanter is a large, irregular, quadrilateral eminence which projects from the angle of the junction between the neck of the femur and the body. The lesser trochanter is a conical imminence which projects posteriorly from the base of the neck. An intertrochanteric line runs obliquely from the greater trochanter to the lesser trochanter on the anterior surface of the femur.

Because of the affects of age, injury and/or disease, patients all too frequently require hip replacement. In such a surgical procedure, the prosthetic cup-shaped device, generally composed of a high molecular weight polyethylene (sometimes supplemented by a metallic shell), is fixed into the acetabulum with use of bone cement or by other mechanical means, and the replacement of portions of the femur with the usually metallic "ball and stem" device, stem portion of which fixed into the femur with either cement or other mechanical means. The prosthetic devices cooperate swivelly to permit articulation between the femur and the hip. As a result, the patient gains mobility of the lower extremity and freedom from pain. During surgery, the proximal portion of the femur comprising the head and neck, are removed, generally by incision above the intertrochanteric line.

In general, the femoral prosthetic device is also composed of corrosion resistant metal alloy. The femoral device includes a head, a neck, and a stem. The stem is adapted for insertion rigidly and securely within an opening formed in the femur, after the femoral head and neck have been surgically removed. The proximal femur os filled with bone cement, then the femoral implant is inserted.

After the acrylic cement solidifies it acts as a filler to firmly secure the implant to the femur. After patient has recovered from the surgical procedure, in successful cases, the patient is able to move about with more freedom and less pain than previously. With such an increasing number of hip replacement surgeries being performed, there is a concomitant increase in failure of the implant. This failure may be caused by infection. However, it is frequently caused by a mechanical loosening between the osseous tissue and implant. Fixation failure is a very serious condition which, in most cases, necessitates early surgical intervention.

Whatever the cause of implant failure, a common characteristic is noted. It is loosening either at the tissue/cement interface, or at the cement/prosthetic stem interface.

When fixation at either interface fails, a serious condition exists, because of the occurrence of movement of the stem in relation to the bone. In such cases, the stem acts as a rasp to abrade the bone tissue. Debris causes inflammation reaction which in turn causes more bone reabsorption. If not diagnosed and corrected early, such abrasion and inflammation can result in such a large amount of bone loss, that subsequent implantation may be impossible, or at least difficult to achieve. In addition to the problem of bone loss experienced in implant failure, the condition, if not corrected, results in great pain for the patient.

Therefore, in order to prevent bone loss due to implant loosening and to alleviate pain caused by a loosened implant, it would be highly desirable to have a method of discovering prosthetic implant fixation failure at an early stage. However, from the diagnostic aspect, it should be noted that pain experienced by the patient is not always a reliable indicator of implant failure, because the pain may be caused by other factors. Thus, a need exists for a reliable method for discovering fixation failure, which method does not depend upon the occurrence of pain in diagnosis.

Generally, two procedures have been utilized in the attempt to diagnose prosthesis implant integrity. One of such procedures is to inspect the bone/implant area by x-ray examination. This technique has several limitations. In the first place, the technique is not entirely accurate, since it frequently fails to identify areas of implant loosening. Additionally, the x-ray technique entails the exposure of the patient to unwanted radiation. In addition, such techniques are generally ineffective in diagnosing implant failure at an early stage. Further, the x-ray use in such a technique presents a health hazard to the patient.

Another technique for attempting to evaluate bone implant fixation integrity utilizes conventional or digital subtraction arthrography methods. These methods are limited, because they utilize a contrast medium which must be introduced in close proximity to the area of cement failure, otherwise the medium does not effectively disclose the failure.

In addition, the arthrographic techniques often produce false negatives. Reliance on such false negatives can lead to injury to the patient. Another important limitation of arthrographic techniques is the fact that it is invasive, causes patient discomfort and, has a risk of introducing infection.

Therefore, it would be highly desirable to have a method and apparatus for determining implant fixation integrity, without the necessity of employing harmful radiation. Also, such techniques should be non invasive, painless and substantially risk free.

Chung et al., (1979) reported a limited anatomical study of the alteration of natural resonant frequency of the femur during curing of the cement. They alluded to the possibility of diagnosing prosthetic loosening by small alterations in the natural resonant frequency of the bone-implant unit in secure and loose prostheses. Van der Perre (1984) reported that in the case of a loose prosthesis, there was a decrease in the resonant frequencies, and that the frequency spectrum was 'rather noisy'. He also proposed that monitoring of the resonant frequencies over time would be the best method of determining loosening of the prosthesis. In previous studies, a considerable variation in the natural resonant frequency of whole cadaver femurs and in femurs with secure prosthetic implants in situ has been observed consistent with the individual differences in the mass and shape of the bones. Hence, if the phenomenon of frequency shift on loosening of the prosthesis is to effectively used, as proposed by Chung and his coleagues and by Van der Perre, prior knowledge of the resonant frequency of the bone-implant unit before loosening has ocurred is required for every patient. This information would not realistically be available in the clinical situation.

A further limitation of the Chung technique is that it is invasive, utilizing a needle driven by a speaker diaphragm. In this regard, in clinical practice, measurements could only be made by using a hypodermic needle brought into contact with the underlying bone. Such a technique would certainly be highly painful and carry the risk of infection.

Therefore, in light of the limitations in the prior known techniques, it would be highly desirable to have a method and apparatus, which would be useful in the dynamic analysis of bone implant composite integrity, in a painless and non-evasive manner. Such a technique would provide reliable clinical data, irrespective of age, bone differences. Further, it would be highly desirable if such a method and apparatus could be developed in such a manner that they could be utilized at any time after prosthetic implantation, without the requirement for acquisition of base-line reference values immediately after implantation surgery.

DISCLOSURE OF INVENTION

It is an object of the present invention to provide a new and improved method and an apparatus for determining the integrity of implants fixation in the bone without the need for the utilization of X-rays, in a noninvasive relatively painless manner.

It is a further object of this invention to provide such a new and improved method and apparatus for determining the integrity of bone implants in such a manner that a determination can be made at any time after surgical implantation, in an absolute manner without the need for prior base-line reference values for comparison.

Briefly, the above and further objects of the present invention are realized by providing a method and apparatus for determining hip implant integrity by detecting loosening of the implant imbedded in a bone of a limb of a patient.

The implant fixation integrity determining apparatus includes a vibrator, which is pressed into engagement with the limb to impart vibratory motion to the bone. The vibrator is controlled to cause the vibratory motion to have a predetermined recurring pattern. A pick-up device is pressed into engagement with the limb spaced from the vibrator, over the same bone near the implant for detecting the vibratory motion transmitted through the bone implant composite to generate an output signal. The recurring pattern of the output signal transmitted through the bone implant composite is analyzed. Implant loosening is determined when the sustained wave superimposition is noted on the oscilloscope and/or significant secondary harmonics are noted on the spectrum analyzer.

Therefore, the present invention provides a noninvasive method and apparatus for determining bone implant fixation integrity. In addition, the inventive technique is substantially risk free and generally painless to the patient. Further, the present invention does not involve the introduction of any harmful radiation, or substances into the body of the patient and, for that reason, may be utilized repetitively with decreased patient risk. Additionally, the inventive apparatus may be used conveniently in the physician's office to monitor limb implant fixation integrity.

BRIEF DESCRIPTION OF DRAWINGS

The above mentioned and other objects and features of this invention and the manner of attaining them will become apparent, and the invention itself will be best understood by reference to the following description of an embodiment of the invention in conjunction with the accompanying drawings, wherein:

FIGS. 2-5 are waveform diagrams useful in understanding the invention.

BEST MODE FOR CARRYING OUT THE INVENTION

Figure 1:
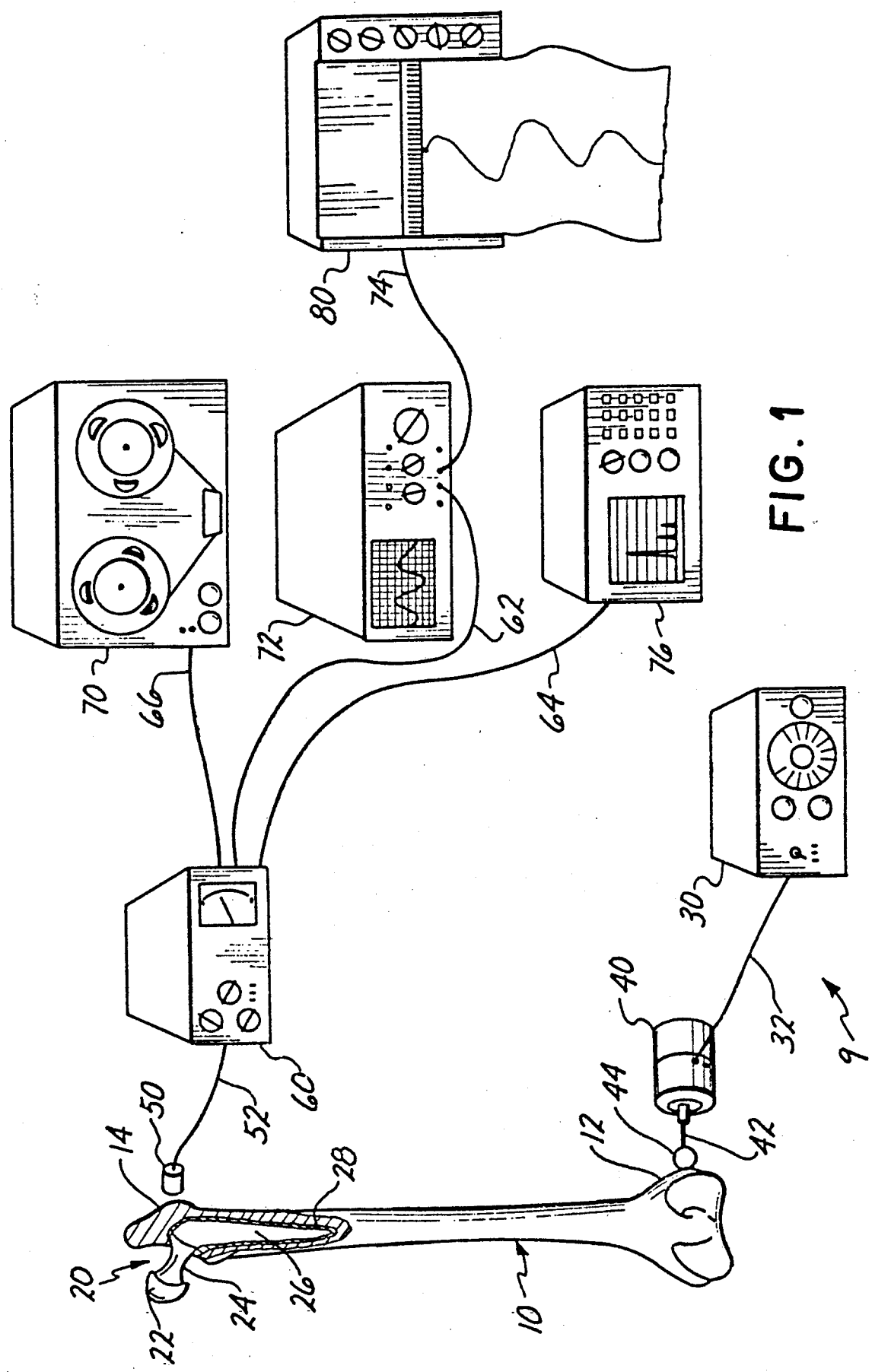

Referring now to the drawing, there is shown an apparatus 9, which is constructed according to the present invention, and which is adapted to perform a limb implant fixation integrity diagnosis. A partially sectioned human femur 10 has a hip replacement prosthesis 20, under test by the apparatus 9, applied at the distal end of the femur. While a bone is shown for illustration purposes, it should be understood that the apparatus 9 is adapted to test a live person, and thus the apparatus 9 comes into contact with the outer skin (not shown) and not directly into contact with the bone.

The apparatus 9 generally comprises a signal generator, such as sine wave generator 30, controls a vibrator 40 to impart vibratory motion to the bone 10 to determine the fixation integrity of the prosthetic implant. Spaced apart from the vibrator 40. A signal pickup device, such as accelerometer 50, receives the vibrations transmitted through the bone implant composites 10, 20, 28. An amplifier 60 enhances the output of the accelerometer 50 to enable the amplified signal indicative of the transmitted vibratory signal to be supplied to an oscilloscope 72 for graphical display purposes. A spectrum analyzer 76 also processes the output of the amplifier 60 to facilitate the analysis of the signal transmitted through the bone implant composite under test. A tape recorder 70 and/or a chart recorder 80 are also used to record the transmitted signals.

Prosthesis implant loosening can be determined when a recurring signal having a predetermined pattern, for example, in the form of a sine wave signal produced by the sine wave generator 30, is imparted to the femur, and the output signal transmitted through the bone implant composite displaying wave superimposition.

This is the case, because the input signal and the output signal are substantially identical (in this example, regular sinusoid pattern without superimposition) in a nonimplanted bone, as well as in a bone in which prosthesis is firmly implanted.

Considering now the generator 30 in greater detail, the signal generator 30 produces the recurring input signal having a predetermined pattern in the form, for example, of a sine wave signal. A generator output cable 32 supplies the input signal to the vibrator 40, which has an arm 42 connected to an enlarged spherical head or tip 44 at its outer distal end. Vibratory motion is imparted at the skin tissue (not shown) surrounding a condyle 12 of the bone 10 by the spherical tip 44.

The spherical tip 44 provides an effective method for imparting vibratory motion to the femur of a patient. In a preferred form of the invention, the spherical tip is about 15 to about 25 millimeters in diameter. In a more preferred form of the invention, the spherical tip 44 is about 19 millimeters in diameter.

Because of its shape and size, spherical tip 44 has a large surface area to engage the skin over a large area. The tip 44 is effective in depressing the skin and underlying muscle of the patient to engage firmly the tissues without causing pain to the patient. Because of its size and shape, the tip 44 is effective in imparting substantially distortion free vibratory motion to the femur in accordance with the present invention.

Referring to the drawing, the hip prosthesis 20 implanted in the femur 10, is conventional and includes a head 22 which is adapted to fit within acetabular cup. A neck 24 interconnects the head 22 and a stem 26.

During hip replacement surgery, the stem 26 is cemented into the femur 10. In a successful surgical procedure, a cement layer 28 provides a firm, uninterrupted interposition between the surfaces of the stem 26 and the bony tissue of the bone 10.

Subsequent to hip implant surgery, the integrity of the bone implant composite can be determined by the present invention. As discussed above, vibratory motion having a predetermined recurring pattern in the form, for example, of a sine wave signal is imparted to the bone 10 at the lateral condyle 12. The signal pickup device 50 is spaced from the lateral condyle and, as depicted in the drawing, is near the greater trochanter 14. The signal from the accelerometer 50 is supplied via an accelerometer output cable 52 to the amplifier 60. After amplification, the signal is transmitted by an oscilloscope input cable 62 to the oscilloscope 72, by means of which the output signal can be analyzed and displayed.

It will be readily clear to one skilled in the art of electronic diagnostic procedures that the output signal from the amplifier 60 can also be transmitted by, for example, an analyzer input cable 64 from the amplifier 60 to an analyzer 76 which is used for further analysis of the output signal In addition, the signal can be transmitted, for example, to the tape recorder 70 by means of a tape recorder input cable 66 whereby the output signal can be stored for later retrieval and analysis.

It will be further apparent to those skilled in the art of utilizing electronic equipment for diagnosis, that the output signal can be transmitted by, for example, a chart recorder input cable 74 from the oscilloscope 72 to the chart recorder 80, in order to obtain an easily readable tracing of the output signal to be used for documentation.

By utilizing the methods and apparatus herein disclosed, replacement hip implantation integrity can be readily determined by analysis of the output signal received via the pick-up device 50, with the input signal supplied from the generator 30. In cases where successful implantation has occurred and a firm implant fixation has resulted, the output signal will demonstrate a pure tone without wave superimposition. Where a sustained wave superimposition is observed, a diagnosis of a loose prosthesis can be made.

The method and apparatus herein disclosed have been utilized in both in vitro and in vivo tests. In the in vitro tests, femurs derived from cadavers were utilized while, for the in vivo tests, the integrity of hip implantations in living patients was performed.

Following are examples of the in vitro and in vivo tests of the present invention.

EXAMPLE I — IN VITRO TESTS

Ten fresh cadaver femurs were obtained from postmortem specimens and deep frozen until required. Specimens were taken from patients in the age group 31–82 years and known to be free from pathological bone disorders. The specimens were obtained from six females and four males and comprised equal numbers of right and left femurs. After defrosting, the bone was supported by clamping each end in resilient plastic foam in an attempt to simulate anatomical supports. A vibration of known frequency and power was applied over the lateral aspect of the lateral femoral condyle using a "mini-shaker" vibration apparatus 40 fitted with a 19 mm diameter spherical tip 44 and driven by a sine-wave generator 30.

Care was taken to ensure firm contact with the bone as intermittent contact gave rise to distortion of the signal due to rattling between the vibrator and hard bone surface. The output was recorded using a PCB Piezotronics 303A03 low mass accelerometer 50 applied to the greater trochanter and connected, through an amplifier 60, to a digital storage oscilloscope 72 and an X-Y plotter 80. The input frequency was scanned from 100–1000 Hz, and the resonant frequency was determined. The output waveform was studied and recorded throughout the frequency range.

A Charnley femoral prosthesis was then cemented in standard fashion, and vibration testing of the femur with the prosthesis firmly implanted was repeated. The femoral implant was then deliberately loosened at the cement-implant interface. This was achieved by removal of a small amount of proximal cement 28 and separation of the implant from its cement mantle (cement layer). The vibration testing was again performed. A frequency analysis was obtained in both the above groups using the spectrum analyzer 76.

A further experiment was performed on five of the femurs where cement/bone interface loosening was simulated by allowing the cement mantle to cure on a prosthesis before inserting it in a prepared femur. All of these cases underwent similar vibration testing and frequency analysis of the output signal.

IN VITRO RESULTS

In intact cadaveric femurs, a sinusoidal output waveform was observed on the oscilloscope. Harmonic content, as detected by the spectrum analysizer, was a small percentage of the primary signal. There was considerable variation in the natural resonant frequency of the specimens, determined as the excitation frequency at which the amplitude of the output signal was seen to reach a maximum. The natural resonant frequency of intact cadaveric femurs varied from 220 to 375 Hz, with a mean of 302 Hz, and was unaffected by repositioning in the plastic foam clamps (not shown). With a firmly implanted femoral prosthesis in situ, the natural frequency varied from 230–325 Hz (mean = 293 Hz).

Figure 2:
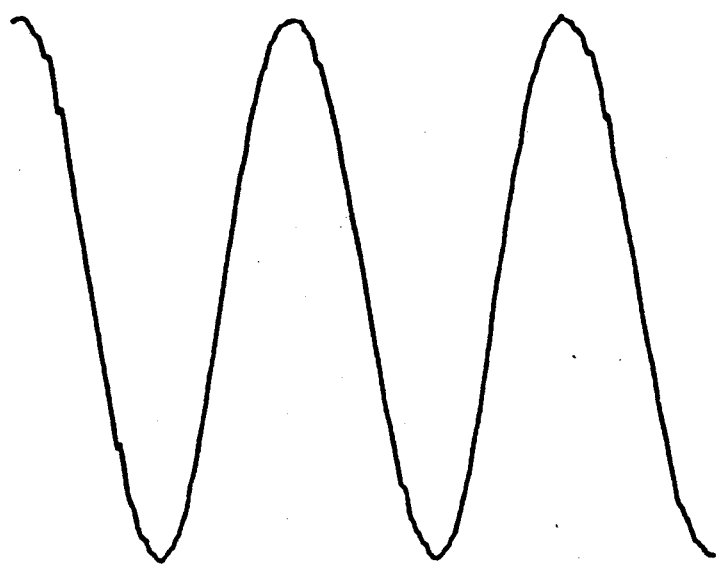
FIG. 2 is a diagrammatic, fragmentary representation of a hip implant fixation integrity determining apparatus, which is constructed in accordance with the present invention.
Figure 3:
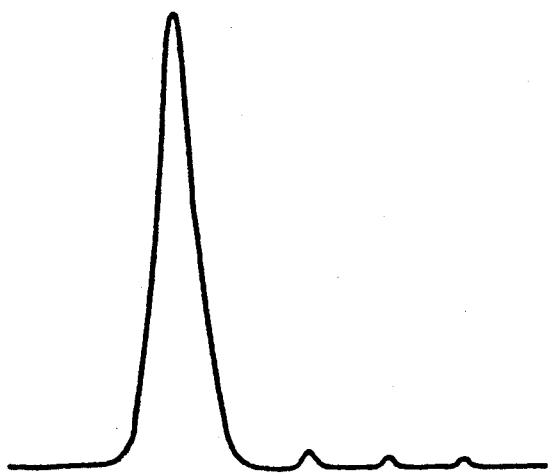

Markedly differing output waveforms were observed between the cases of firmly implanted and loose femoral implants (at both the prosthesis/cement and bone/cement interfaces). Where the prosthesis was firmly cemented, the application of a vibration throughout the frequency range (100–1000 Hz) consistently produced a visibly regular sinusoidal output in all the specimens tested (FIG. 2). Frequency analysis of this output demonstrated that it was a pure tone with no significant superimposed harmonics (FIG. 3).

Figure 4:
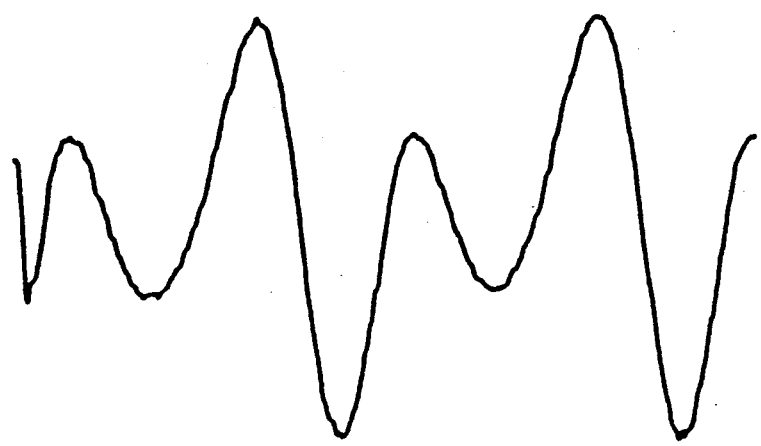
Figure 5:
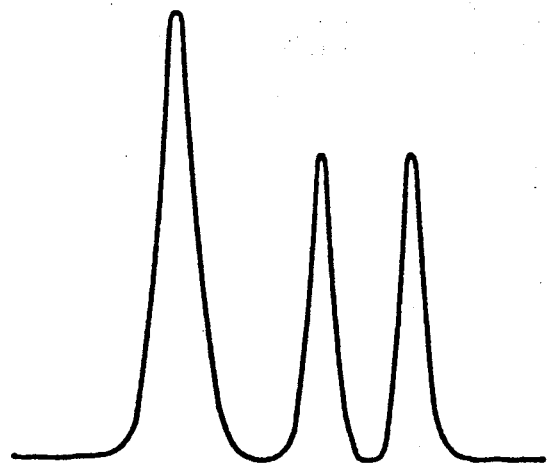

In the groups of loose prostheses (at the bone/cement and prosthesis/cement interface) the applied vibration produced, in every case, an output signal displaying distinct and sustained wave superimposition (FIG. 4). For each femur this pattern of distortion was observed over a narrow frequency band within a few tens of Hz about the resonant frequency. When this signal was frequency analyzed, the magnitude of the secondary harmonics relative to the primary frequency was observed to be markedly increased (FIG. 5).

EXAMPLE 2 — IN VIVO TESTS

To test the efficacy of the vibration technique as an in vivo diagnostic tool, a number of in-patients were examined. Seven of these patients (with ages ranging from 76–85 years, mean = 80 years) had been admitted for revision on the basis of symptomatic "loosening" of the prosthesis. Subsequently, four of these subjects had aspiration arthrograms performed pre-operatively. At surgery, the adequacy of fixation of the femoral component was assessed. A further four patients who were approximately two weeks following total hip replacement were also tested.

During testing, the patient was placed in the lateral position with the test hip uppermost. The vibration signal was applied over the lateral femoral condyle, just above the joint line and output signals were recorded using the accelerometer placed over the greater trochanter. The output signals were recorded, displayed and processed as described above. Although the vibration signal was applied and detected through a significant thickness of flesh, an adequate output signal was obtained. The maximum power applied was 0.5 watts. The patients reported no feelings of discomfort.

IN VIVO RESULTS

Seven patients underwent revision surgery for symptomatic "loosening." In five cases a loose femoral prosthesis was demonstrated at operation. In all five of these cases, the vibration test was positive, showing distortion of the waveform. Four patients underwent pre-operative arthrograms, two of which were falsely negative. In the remaining two cases, although clinical evaluation and plain X-rays were suggestive of loosening, both vibrometry and arthrogram were negative. The femoral components were found to be securely fixed at operation. In the four cases tested two weeks after total hip replacement, no output distortion was observed.

While a particular embodiment of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A method for determining, without the utilization of base line information, the integrity of a heterogeneous composite substrate of an implant fixation in a bone of a limb of a patient, the substrate including a bone to cement interface and a cement to implant fixation interface, comprising:

using a vibrator having a smoothly contoured member;

compressing firmly with the contoured member, the flesh of the limb to the bone and to the implant fixation, of the substrate, over a large outer surface area of the limb, to enable vibrations to be imparted through the compressed flesh and through said heterogeneous composite substrate, to the bone, with little discomfort or damage to the limb;

supplying to said vibrator an input energizing electrical signal having a predetermined recurring pattern of a single non-resonant frequency;

vibrating the heterogeneous composite substrate, including each one of the interfaces thereof in response to the vibrator being energized by said input signal;

using a single pick-up device;

pressing the pick-up device into engagement with the outer surface of the limb spaced from the vibrator at the same bone, for detecting the vibratory motion of the bone implant heterogeneous composite substrate, to generate a single output electrical signal;

analyzing said input energizing electrical signal relative to the recurring pattern only of the single output electrical signal transmitted through the bone implant heterogeneous composite substrate and each one of said interfaces, without the utilization of base line information; and determining implant loosening when said recurring pattern of said output signal is persistently distorted.

2. An apparatus for determining, without the utilization of base line information, the integrity of a heterogeneous composite substrate of an implant fixation in a bone of a limb of a patient, the substrate including a bone to cement interface, and a cement to implant fixation interface, comprising:

vibrator means for imparting to the heterogeneous composite substrate, including each one of the interfaces thereof, vibratory motion having a predetermined recurring pattern, said vibrator means including a smoothly contoured member adopted to compress firmly the flesh of the limb to the bone and to the implant fixation, of the substrate, over a large outer surface area of the limb, to enable vibrations to be imparted through the compressed flesh and through said heterogeneous composite substrate, to the bone, with little discomfort or damage to the limb;

means for generating a vibrator energizing electrical signal having a predetermined recurring pattern of single non-resonant frequency;

single pick-up means adapted to be pressed into engagement with the outer surface of limb spaced from said vibrator means for detecting the vibratory motion of said bone implant heterogeneous composite substrate, to generate a recurring single output electrical signal; and means for analyzing said input energizing electrical signal relative to the pattern of said single output electrical signal only transmitted through the bone implant heterogeneous composite substrate and each one of said interface, without the utilization of base line information, to determine implant fixation loosening when said single input recurring pattern is persistently distorted;

wherein said means for analyzing includes means for detecting subharmonic frequencies of said signal output signal to indicate a lack of implant fixation integrity.

3. An apparatus of claim 2, wherein said vibrator means includes a spherical head for engaging the limb, and means for vibrating said head.

4. An apparatus of claim 3, wherein said spherical head is between about 15 mm and about 25 mm in diameter.

5. An apparatus of claim 4, wherein said diameter is about 19 mm.

6. An apparatus of claim 2, wherein said signal generator means is a sine wave generator.

7. An apparatus of claim 2, wherein said pick-up device means is an accelerometer.

8. An apparatus of claim 2, further including an amplifier coupled to the output of said pick-up means.

9. An apparatus of claim 2, further including a spectrum analyzer means for analyzing the signal received via said pick-up means.

10. An apparatus of claim 2, wherein said means for analyzing the pattern of the single output electrical signal only includes an oscilloscope for analyzing the presence or absence of sustained wave superimposition.

11. An apparatus of claim 10, further including a chart recorder.

12. An apparatus of claim 2, wherein said means for analyzing the pattern of the single output electrical signal only is a spectrum analyzer said spectrum analyzer being adapted for analyzing the presence or absence of significant secondary harmonics in an output signal.

13. An apparatus of claim 12, further including an oscilloscope for displaying graphically said output signal.

* * * * *

UNITED STATES PATENT AND TRADEMARK OFFICE
CERTIFICATE OF CORRECTION

PATENT NO. : 5,024,239
DATED : 6/18/91
INVENTOR(S) : ROSENSTEIN

It is certified that error appears in the above-identified patent and that said Letters Patent is hereby corrected as shown below: In The Abstract delete "generae" and substitute therefor --generate--.

Column 3 Line 17, delete " coleagues", and substitute therefor --colleagues--.

Column 4 Line 27, delete "Fig.2", and substitute therefor --Fig.1--.

Column 5 Line 58, after " output signal", insert --.--.

Column 8 Line 54, delete "adopted" and substitute therefor --adapted --.

Signed and Sealed this

Twenty-second Day of December, 1992

Attest:

DOUGLAS B. COMER

*Attesting Officer*   *Acting Commissioner of Patents and Trademarks*